United States Patent [19]

Juge

[11] Patent Number: 4,983,768

[45] Date of Patent: Jan. 8, 1991

[54] PROCESS OF PREPARATION OF PHOSPHINAMIDES APPLICATIONS AND NEW PRODUCTS

[75] Inventor: Sylvain Juge, Puteaux, France

[73] Assignee: Societe Nationale Elf Aquitaine, France

[21] Appl. No.: 754,956

[22] Filed: Jul. 15, 1985

Related U.S. Application Data

[63] Continuation-in-part of Ser. No. 448,370, Dec. 9, 1982, abandoned.

[30] Foreign Application Priority Data

Dec. 11, 1981 [FR] France ................................. 8123153
Dec. 3, 1982 [FR] France ................................. 82 20264

[51] Int. Cl.$^5$ ............................................. C07F 9/02
[52] U.S. Cl. ....................................... 564/12; 558/104
[58] Field of Search .................. 564/12; 750/971, 969; 558/104

[56] References Cited

PUBLICATIONS

Fujisawa et al., *Bulletin of the Chemical Society of Japan*, vol. 40 pp. 147–149 (1967).

Koizumi et al., *Tetrehedron Letters*, vol. 22, pp. 511–572 (1961).

*Primary Examiner*—Charles F. Warren
*Attorney, Agent, or Firm*—Ostrolenk, Faber, Gerb & Soffen

[57] ABSTRACT

Phosphinamides are prepared by the action of an organic halide on an oxazaphospholidine. Depending upon the configuration desired for the stereoisomer to be obtained, an oxazaphospholidine is utilized which has been derived from a (+) or (−) optically-active amino-alcohol. These phosphinamides are useful for the preparation of phosphinates, in particular optically-active phosphinates of known absolute configuration; for this, the phosphinamide is subjected to alcoholysis.

14 Claims, No Drawings

PROCESS OF PREPARATION OF PHOSPHINAMIDES APPLICATIONS AND NEW PRODUCTS

This is a continuation-in-part of application Ser. No. 448,370, filed Dec. 9, 1982, now abandoned.

The present invention relates to a new process for the production of phosphinamides; it comprises certain phosphinamides as new chemical products. The invention relates to the utilization of phosphinamides in the preparation of various organic compounds of phosphorous, among which the phosphinates have a particular importance. A marked advantage of the invention is that it makes possible the preparation of various optically-active compounds with good yields and with high optical purity.

The utility of phosphorus-containing organic compounds and in particular optically-active compounds is well-known at present. It is known that many natural and synthetic products can now be prepared by asymmetric synthesis, catalysed by means of transition metals and particularly by catalysts comprising optically-active organo-phosphorus ligands. Substances of interest in agriculture, foodstuffs, pharmacy and perfumery are thus prepared. The production of L-DOPA, so useful in therapeutics, in particular for the treatment of Parkinson's disease, is an example. The development and study of these syntheses are limited at present by difficulty in preparing optically-active organo-phosphorus ligands, which are very often employed in asymmetric catalysts.

The present invention relates to an improvement in this technique, rendering possible easier and more economical synthesis of a whole series of organo-phosphorus compounds, particularly phosphinamides and, from them, phosphinates, phosphine oxides, phosphines, phosphoniums, phosphinimides etc.

By starting with phosphinates, it is simple to obtain the various produce indicated above. It is thus important to be able to produce phosphinates in a more economical manner than heretobefore. The methods of the prior art are quite laborious; thus, that of Mislow, De Bruit et coll. (Journ. Am. Chem. Soc. 91, 7393, 1969 and J. Org. Chem. 37, 2272-1972) operate through the intermediary of methyl phosphinate, starting from a dichlorophosphine with division into two of the phosphinates, the whole of the process comprising 7 stages. Another synthesis route for optically-active phosphinates utilizes as the starting material 1,3,2-oxazaphosphole (Tetrahedron Let. 571, 1980); it also necessitates division into two of the oxazaphospholes and the use of organo-metallic reagents, the whole of the operations comprising 4 stages. In a general manner, the processes utilized at present give a poor final yield of phosphinates, they are lengthy, they necessitate a more or less difficult division into two of the intermediates and require the use of an industrially-obtainable key intermediate product which has two of the desired phosphinate substituents; in these processes, the choice of the third substituent of the phosphinate is also limited.

The new process according to the invention, which utilizes a phosphinamide by a reaction in a single stage, allows access to all desired phosphinates by alcoholysis, which can be effected readily and under economic conditions. The preparation of phosphinamides according to the invention may be effected very rapidly, namely in 15 minutes, with industrially acceptable yields; it may also be conducted more slowly and give greater yields. About 1 hour generally suffices to pass from the amide to the corresponding phosphinate. The intermediates of the process have good chemical stability; reagents or reactions which are complex are not required, nor are severe operative conditions. Another substantial advantage, for the synthesis of optically-active products, is the very elevated asymmetric induction.

The process according to the invention consists in preparing a phosphinamide by the action of an organic halide on oxazaphospholidine, and it is characterized in that it is carried out secure from air and humidity, and preferably in the absence of light. This reaction can be represented as follows:

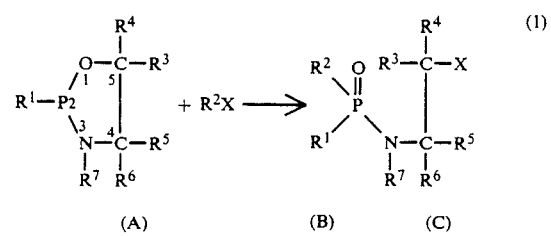

In the above formulae, the symbols $R^1$ and $R^3$ to $R^7$ designate hydrocarbon groups or hydrogen atoms. These groups are the same or different and, in particular can be aliphatic, cycloaliphatic and/or aryl. Preferably, when $R^3$ and/or $R^6$ are hydrocarbon groups, $R^4$ and $R^5$ represent hydrogen atoms. Among the $R^1$ and $R^3$ to $R^7$ substituents, the most common are $C_1$ to $C_4$ alkyls, phenyl and benzyl; however, alkyls, for example $C_1$ to $C_{18}$, cyclopentyls, cyclohexyls, phenyls substituted by alkyls, naphthyls etc., can also be present. $R^2$ is an alkyl, aralkyl, cycloalkyl, aryl or saturated chain carrying functions such as ester, ether, ketone, etc.

In a preferred embodiment of the invention, the reaction is carried out in obscurity. This is particularly desirable when the reagents are dissolved in a solvent.

According to one operative mode, the oxazaphospholidine A is taken in the solid state and heated with a liquid alkyl, cycloalkyl or aryl halide, B; the phosphinamide C formed is crystallized from an appropriate solvent or separated in an oily form.

This new reaction, which provides the phosphinamide in a suitable yield, is particularly surprising as it has not previously been realized that it could give such a result. In fact, authors who have attempted to apply it working in solution in toluene or some other solvent have only been able to use it for polymers or have obtained badly-defined non-identifiable products (Arbuzov et coll. (Akad. Nauk. SSSP otd Kim. Nauk. 789, 1952)) or Mukaiyama et coll. (Bull. Chem. Soc. Jap. 40, 147, 1967). In contrast therewith, good results are obtained according to the invention, due to the absence of humidity and oxygen (and preferably light) in the reaction zone of an oxazaphospholidine with an organic halide.

The reaction permits of preparing phosphinamide less or more rapidly when the temperature has a value of about 40° to about 100° C. When it is worked at lower temperatures, such as 10° to 40° C., and particularly at ambient temperatures, especially between 15° and 30° C., the reaction is slower but yields and purities are higher.

Following a first embodiment of the invention, solid oxazaphospholidine (A) is heated to a desired temperature, within an inert gas atmosphere, in obscurity, secured from humidity; the appropriate organic halide (B), $R^2X$, is added in excess to it and heating is continued during the time required. Yields of the order of 60% in phosphinamide may thus be obtained, and they are very good in comparison with those of known methods.

Following another embodiment of the invention, the oxazaphospholidine and the organic halide are first dissolved in an appropriate solvent, and the solution is kept at desired temperature, in an inert atmosphere, free from humidity, in obscurity, until a maximum of phosphinamide is formed.

Various conventional solvents are suitable, such for instance as aromatic, aliphatic, cycloaliphatic hydrocarbons or others. Particularly useful are mixtures of benzene hydrocarbons with cyclanes.

The starting material, oxazaphospholidine A, is a substance readily obtainable in good yields by processes known in the art, particularly by the action of a diamino-phosphine on an amino-alcohol. For example, by the method described by Ternaki Mukaiyama and Yasuto Kodaira (Bull. Chem. Soc. Japan 39, (6), 1287–301 (1966)), 1,3,2-oxazaphospholidines are obtained by the action of diamino-phosphine on an amino alcohol which, in the present case, can be ephedrine. The reaction can be shown diagrammatically in the following fashion:

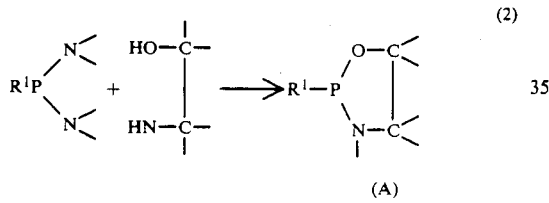

(A)

A diastereoisomer of this oxazaphospholidine can be given by the reaction indicated above, if an optically-active amino-alcohol is used. An unexpected advantage of the invention lies in the fact that, starting from such an oxazaphospholidine by the action of the halide (B), a phosphinamide (C) is obtained with a very good preservation of the diastereoisometric purity. Thus, starting with (−) ephedrine as the amino-alcohol, this assists in the practical formation of a single one of the possible diastereoisomers of oxazaphospholidine; the absolute configuration with respect to the phosphorus atom is thus fixed.

As regards the possible transformations of the phosphinamides obtained by the process of the invention, the most important is alcoholysis which allows easy passage to the corresponding phosphinates according to the reaction:

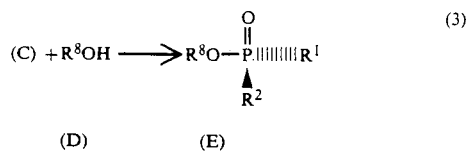

It can be seen that the process of the invention allows selection as desired of the radicals $R^1$, $R^2$ and $R^8$ for the desired phosphinate E. In fact, $R^1$ is derived from the initial oxazaphospholidine A, $R^2$ is given by the halide, B, while $R^8$ depends on the choice of alcohol or phenol employed for the alcoholysis in the reaction (3).

A particular manner of carrying out the alcoholysis, according to the invention, consists in catalysing the reaction with an ion exchange resin; this brings about the advantage of facilitating the separation of the catalyst by mere filtration after alcoholysis.

The advantage indicated above of being able to prepare the phosphinamide C from an optically-active oxazaphospholidine A is reflected in the production of phosphinates according to the reaction (3). In fact, within the scope of the invention, it is possible to obtain phosphinates corresponding to the two antipodes of the known absolute configuration, namely:

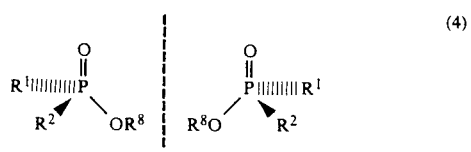

According to the conventions, by the above notation, $R^2$ is located above the page and $R^1$ below, while 0 and $OR^8$ are in its plane. The antipodes of the absolute configuration R or S determining the phosphinate E can be obtained respectively by the use of the (+) or (−) aminoalcohol in the reaction (2) yielding the oxazaphospholidine. This result can also be obtained by introducing the groups $R^1$ and $R^2$ in a different order. The following Table of Formulae illustrates these possibilities.

Oxazaphospholidine starting from (−) ephedrine:

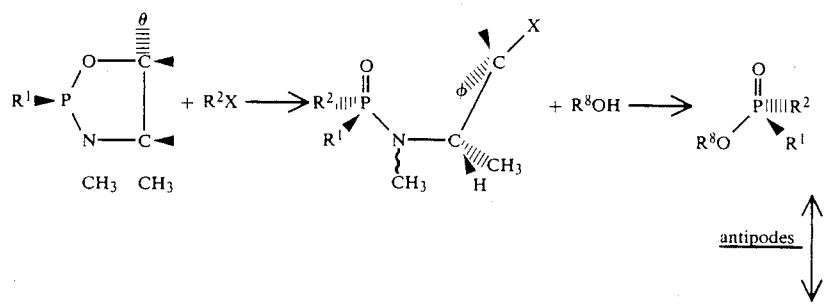

antipodes

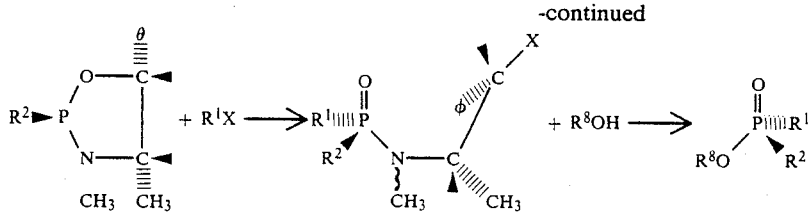

Oxazaphospholidine starting from (+) ephedrine:

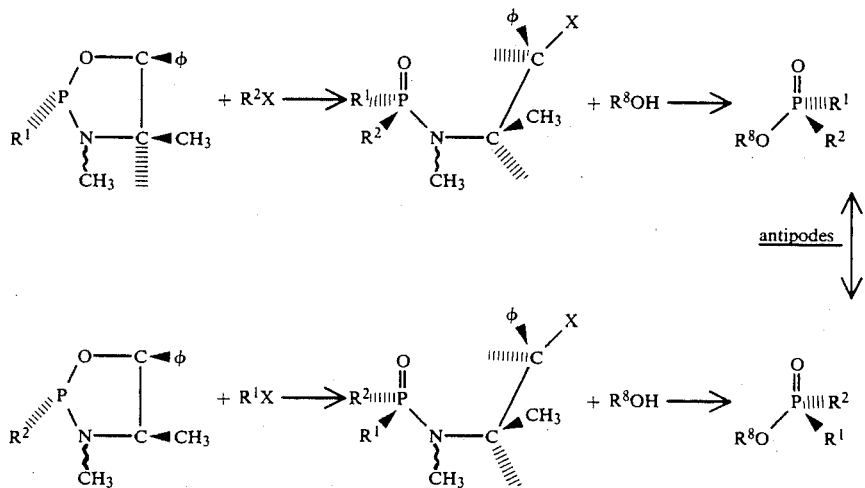

While the preparation of the oxazaphospholidines according to the reaction (2) is known as such and it is already known to effect the alcoholysis (3) of phosphinamides in order to convert them into phosphinates, the combination of the process of the invention (1) with these two reactions forms a three-stage assembly of considerable interest for obtaining phosphinates. Depending upon the nature of the compounds utilized, the yield of each of these stages is about 60% to 100% and the durations are about 12 hours for the reaction (2), ¼ hour for the conversion (1) and of the order of 1 hour for stage (3).

The non-limitative examples which follow illustrate the invention.

EXAMPLE 1

In view of the importance of oxazaphospholidines for the preparation of phosphinamides according to the invention, the manner of operating to obtain one of these phospholidines, namely (+) 3,4-dimethyl-2,5-diphenyl-1,3,2-oxazaphospholidine (2R, 4S, 5R), is described below:

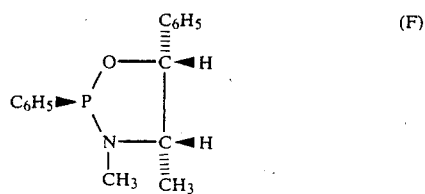

(F)

This is the compound A of the equation (1) given above in which $R^1$ and $R^4$ are phenyls, $R^3$ and $R^5$ are hydrogen atoms, while $R^6$ and $R^7$ are methyls. This is a new compound which has not previously been described in technical literature.

The preparation is effected in a three-necked 1 liter flask provided with an agitator and 2 nozzles for the introduction and removal of a nitrogen sparge. In this way, the amine liberated during the reaction is separated from the medium and can be measured in a washing flask.

0.1 mole of (−) ephedrine is reacted with 0.1 mole of bis(diethylamino)-phenyl-phosphine for 12 hours in 500 ml of toluene between 100° and 110° C. under a light nitrogen stream.

After this time, the reaction mixture is transferred to an evaporation bottle and the volume of the solvent is adjusted to about 250 ml. By simple cooling under nitrogen, the product indicated above precipitates. After filtration and a new partial evaporation of the mother liquor, another fraction of the compound is also recovered.

The overall yield of the crystalline product is 70%; the product melts at 100° C. and can be re-crystallized from toluene; it is stored in a sealed receptacle in the refrigerator.

The NMR spectrum of the crude product of the reaction indicates a very good chemical and diastereoisometric purity.

The following parameters were found:

| NMR $^1$H ($C_6D_6$) | doublet | (3H) | 0.5 ppm |
|---|---|---|---|
| " | " | | 2.4 ppm |
| | multiplet | (1H) | 3.1 ppm |
| | doublet | (1H) | 5.4 ppm |
| | multiplet | (10H) | 7.7–8 ppm |
| NMR ($C_6D_6$) $^{31}$P | | | $\delta = +139.7$ ppm |
| NMR (THF) $^{31}$P | | | $\delta = +141.6$ ppm |

-continued

| Analysis: | C % | H % | N % | O % | P % |
|---|---|---|---|---|---|
| theory | 70.84 | 6.69 | 5.16 | 5.90 | 11.42 |
| found | 70.69 | 6.66 | 5.27 | 5.65 | 11.50 |

Rotational Power: $[\alpha]_D^{22} = +40° \pm 5°$  c = 2.3($C_6H_6$)

EXAMPLE 2

Preparation of (−) 3,4-dimethyl-2,5-diphenyl-2-oxo-1,3,2-oxazapholidine (2R, 4S, 5R)

3 g of the oxazaphospholidine (F) of Example 1 in solution in 50 ml of toluene is left under agitation for 2 days in non-stoppered flask. After this time, the toluene has evaporated and the residue is taken up on acetone. Diisopropyl ether is then added hot (about 50° C.), up to the limit of solubility. The total volume of solvent must not be too large (about 20 ml). By cooling, the expected oxide precipitates. The recrystallization solvent is also an acetone/diisopropyl ether mixture.

In the case of non-precipitation of the product, it is necessary to chromatograph the residue obtained by oxidation on a Merck No. 7734 type silica column eluant 8/2 ether/acetone. The product leaves with an rf of 0.7, which corresponds in general to about 10 100 ml fractions.

This preparation has been effected to verify the configuration of the compound F; in fact, the oxo derivative

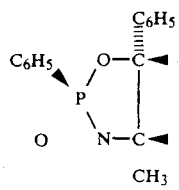

has been described by D B Cooper et al, Tet. Lett. 2697 (1974) and as its absolute configuration is thus known; its production starting from compound F confirms the configuration proposed above for compound F. The melting point found is 161° C.

By heating in air for 24 hours, an oxidized compound is obtained with a yield of 90%.

| NMR $^1H$ (CDCl$_3$) | gives: | | |
|---|---|---|---|
| | doublet | (3H) | 0.91 ppm |
| | " | " | 2.62 ppm |
| | multiplet | (1H) | 3.76 ppm |
| | triplet | (1H) | 5.76 ppm |
| | multiplet | (10H) | 7.2–8. ppm |
| NMR $^{31}P$ (CDCl$_3$) | δ = 33 ppm | | |

EXAMPLE 3

Preparation of (+) N-methyl-N-(1-methyl-2-iodo-2-phenyl)-ethyl(1S, 2S)P-methyl-P-phenyl-phosphinamide (R).

The compound is obtained by the action of methyl iodide on the pholidine F described in Example 1.

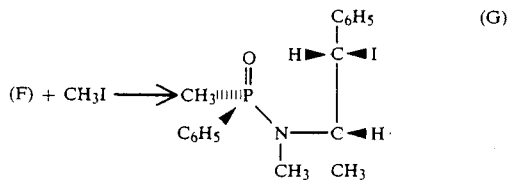

The phosphinamide G corresponds to the formula C in which $R^2$, $R^6$ and $R^7$ are methyls, $R^1$ and $R^4$ are phenyls and $R^3$ and $R^5$ are hydrogen atoms, the halogen X being iodine.

The preparation is effected according to the following operative mode: 0.1 mole of the oxazaphospholidine F in the solid state is heated for 10 minutes at 95° to 100° under nitrogen, in a wide-mouthed filtration tube. An excess (0.3 to 0.4 mole) of methyl iodide heated to the boiling point also under nitrogen is then rapidly added. The practically instantaneous reaction is allowed to proceed for 5 to 10 minutes. By cooling, the expected product crystallizes, provided there is not too much iodide in excess. However, the latter is eliminated easily by evaporation. The residue, whether or not it is crystallized is taken up in hot acetone and taken to the limit of solubility by diisopropyl ether (total volume of solvent 200 ml). By cooling, the desired product precipitates; yield 60%.

The melting point of the product obtained is 160° to 162° C.

| NMR $^1H$ (CDCl$_3$): | doublet | (3H) | 1.1 ppm |
|---|---|---|---|
| | " | " | 1.95 ppm |
| | " | " | 2.45 ppm |
| | multiplet | (1H) | 4.30 ppm |
| | doublet | " | 5.15 ppm |
| | multiplet | (10H) | 7.1–8.20 ppm |

| Elementary Analysis: | | | | | | |
|---|---|---|---|---|---|---|
| | C % | H % | N % | O % | P % | I % |
| theory | 49.41 | 5.20 | 3.39 | 3.87 | 7.50 | 30.70 |
| found | 49.63 | 5.29 | 3.35 | 3.87 | 7.54 | 30.57 |

$[\alpha]_D^{21} = +162.5°$   c = 2.5(CH$_3$OH)
NMR $^{31}P$ (CDCl$_3$) δ = +35.1 ppm

EXAMPLE 4

Preparation of (+) N-methyl-N-(1-methyl-2-iodo-2-phenyl)-ethyl(1S,2S)P-methyl-P-phenyl-phosphinamide (R).

This is an analogue of the phosphinamide G of Example 3 in which the methyl on the phosphorus atom is replaced by an ethyl. This compound is prepared from the phospholidine F of Example 1 by an operation similar to that of Example 3, the methyl oidide being replaced by ethyl iodide. Heating under reflux at 70° takes place for 8 minutes.

The crude product of the reaction, after evaporation of the halide, is subjected to chromatography on alumina with ethyl acetate as the eluant. The expected phosphinamide is recovered after ten 100 ml fractions. The product has the form of a thick oil. Its configuration is the same, that is to say (R)$_p$, as that of the compound G described in Example 3.

| NMR $^1H$ (CDCl$_3$) examination indicates: | | |
|---|---|---|
| doublet | (3H) | 1.1 ppm |
| triplet | " | 1.25 ppm |

| | | | |
|---|---|---|---|
| multiplet | (2H) | | 2.40 ppm |
| " | " | | 2.10 ppm |
| " | (1H) | | 4.20 ppm |
| doublet | (1H) | | 5.25 ppm |
| multiplet | (10H) | | 7.2–8.25 ppm |
| Micro-analysis: | C % | H % | N % |
| calculated | 50.60 | 5.43 | 3.28 |
| found | 50.48 | 5.54 | 3.24 |
| $[\alpha]_D^{21} = +116°$ | | c = (CHCl$_3$). | |

EXAMPLE 5

Preparation of (+) N-methyl-N-(1-methyl-2-bromo-2-phenyl)-ethyl(1S,2S)P-benzyl-P-phenyl-phosphinamide (R).

The desired product is a phosphinamide analogous to that of formula C of reaction (1); it is a substance in which $R^1$ is a phenyl, $R^2$ is a benzyl, $R^3$ is a hydrogen atom, $R^4$ is a phenyl, X is a bromine atom, $R^5$ is a hydrogen atom and $R^6$ and $R^7$ are methyls.

The preparation consists of heating 0.1 mole of the oxazapholidine F of Example 1 at 90° C. under nitrogen and rapidly adding 8 moles of benzyl bromide maintained at the same temperature, also under nitrogen. The reaction is allowed to proceed for 10 minutes.

After cooling and evaporation under vacuum of the excess benzyl bromide, the residue is taken up in hot acetone. On cooling, crystals of a mixture of the diastereoisomers of the phosphinamide formed are deposited. With this halide in fact and under the operative conditions indicated above, some degree of epimerisation around the phosphorus atoms is confirmed.

After filtration and evaporation of the acetone, the residue is chromatographed on basic alumina at the rate of 3 g per 100 g of Al$_2$O$_3$. The phosphinamide leaves after 10 50 ml fractions and the NMR analysis revealed a correct diastereoisometric purity. For the more abundant diastereoisomer of the configuration (R)$_p$, this gives the following indications:

| NMR $^1$H (CDCl$_3$) | doublet | (3H) | 1.05 ppm |
|---|---|---|---|
| | " | " | 2.50 ppm |
| | multiplet | (2H) | 3.65 ppm |
| | " | (1H) | 4.30 ppm |
| | doublet | (1H) | 5.05 ppm |
| | multiplet | (15H) | 7–8.2 ppm |

The mixture of diastereoisomers isolated by crystallization has a melting temperature of 180°–183° C.

NMR $^1$H(CDCl$_3$)

| | | |
|---|---|---|
| doublet (3H) | 0.65 ppm | |
| doublet (3H) | 1.05 ppm | |
| triplet (3H) | 2.55 ppm | |
| multiplet (1H) | 3.65 ppm | |
| multiplet (1H) | 4.30 ppm | |
| otherwise | | |
| doublet (1H) | 5.05 ppm | |
| doublet (1H) | 4.85 ppm | |

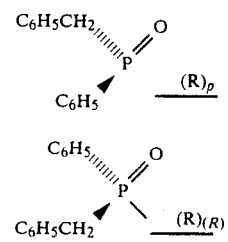

| Analysis: | C % | H % | Br % | N % | O % | P % |
|---|---|---|---|---|---|---|
| calculated: | 62.45 | 5.70 | 18.06 | 3.17 | 3.62 | 7.00 |
| found: | 62.81 | 5.80 | 17.94 | 2.83 | 3.76 | 7.01 |

$[\alpha]_D^{21} = +130°$
c = 1.2(CHCl$_3$)

EXAMPLE 6

A phosphinamide analogous to that of Example 5, but having a chlorine atom in place of the bromine atom, is prepared.

The preparation takes place as in the foregoing case, but with benzyl chloride which gives a diastereoisometric purity of 80/20. Crystallization of the mixture of diastereoisomers from acetone eliminates the major part of the epimer.

After evaporation of the solvent, the residue obtained is subjected to chromatography on basic alumina (3 g per 100 g of alumina; eluent:ethyl acetate). The diastereoisomer leaves after 10 50 ml fractions. The main diastereoisomer prepared, of the configuration (R)$_p$, has a melting point of 154° to 157° C.

| The NMR (CDCl$_3$) gives: | | |
|---|---|---|
| doublet | (3H) | 1.05 ppm |
| " | " | 2.50 ppm |
| multiplet | (2H) | 3.60 ppm |
| " | (1H) | 4.30 ppm |
| doublet | " | 4.95 ppm |
| multiplet | (15H) | 7.20–8.00 ppm |

$[\alpha]_D^{21} = +130°$ c = CHCl$_3$ NMR $^{31}$P(CDCl$_3$) $\delta = +36.34$ ppm

| Analysis: | C % | H % | Cl % | N % | O % | P % |
|---|---|---|---|---|---|---|
| calculated | 69.42 | 6.33 | 8.91 | 3.52 | 4.02 | 7.78 |
| found | 68.55 | 6.43 | 8.69 | 3.43 | 4.54 | 7.17 |

The mixture of diastereoisomers isolated by crystallization (R)$_p$+(S)$_p$, has a melting point of 175° C. Its NMR (CDCl$_3$) indicates:

| doublet | (3H) | 0.55 ppm |
|---|---|---|
| " | " | 1.00 ppm |
| triplet | (2H) | 2.0 ppm |
| multiplet | " | 3.50 ppm |
| " | (1H) | 4.20 ppm |
| doublet | " | 4.80 ppm |
| " | " | 4.95 ppm |
| multiplet | (15H) | 7.00–8.20 ppm |

$[\alpha]_D = +123°$  c = 1.2 CHCl$_3$  NMR $^{31}$P(CDCl$_3$) $\alpha = +36.47$ and +36.21 ppm.

EXAMPLE 7

Application of the phosphinamide of Example 3 (G) to the preparation of methyl methyl-phenyl-phosphinate of the configuration R(+).

290 mg of the phosphinamide are dissolved in 1.76 N methanolic hydrogen chloride solution. After an hour, 10 ml of a 2.8 N methanolic ammonia solution is added to neutralize the acid. After evaporating the solvent and taking up the residue in 10 ml of methylene chloride, this is filtered to eliminate mineral salts. A new evaporation of the solvent gives a residue which is subjected to chromatography on silica with acetone as the eluant (20×20 plates). After extracting with methanol, the band between rf 0.55 and 0.65, the phosphinate formed is recovered.

$[\alpha] = 52°$ c = 3 (benzene, which represents 93% optical purity).

NMR examination has confirmed the structure of this phosphinate known from prior literature (M. J. P. Harguer, Journ. Chem. Soc. Perkin I, 1294 (1979)).

EXAMPLE 8

Application of the phosphinamide of Example 4 for the preparation of methyl methyl-phenyl-phosphinate of the configuration R(+).

500 mg of the phosphinamide are dissolved in 50 ml and 0.15 M methanolic solution of methane-sulphonic acid and the solution is allowed to stand for ½ hour at 60° C. After this time, it is neutralized with 100 ml of a 4M ammonical solution. After evaporation of the solvent, the residue is taken up in 30 ml of methylene chloride and the insoluble mineral salts are separated by filtration. After a new evaporation, the residue is chromatograped on silica with acetone as eluant. The phosphinate formed is recovered after the elution of 10 fractions of about 50 ml. This product, known in the art, is oily and has an $[\alpha]_D = +22.7°$, c=7 (methanol); optical purity=47%. The NMR confirms the structure indicated above.

EXAMPLE 9

Application of the phosphinamide of Example 6 to the preparation of methyl R(−) benzylphenyl-phosphinate.

2.2 g of the phosphinamide is dissolved in 50 ml of an 0.1M methanolic solution of methane-sulphonic acid and the solution is maintained at 55° C. for 2 hours. After neutralization with a 1M methanolic ammonia solution, the solvent is driven off. On taking up in methylene chloride, the residue is filtered and the solvent again evaporated. A filtration on 50 g of alumina for 2 grams gives the phosphinate after several fractions, the eluant being ethyl acetate.

The melting point of the racemate is 96° C. The optically-active phosphinate has a $[\alpha]_D = -3.2°$ for c=6 (methanol), at 77% optical purity.

| The NR (CDCl₃) gives: | doublet | (2H) | 3.3 ppm |
|---|---|---|---|
| | " | (3H) | 3.6 ppm |
| | multiplet | (H) | 7-7.8 ppm |

There is therefore a new phosphinate obtained according to the invention which has not been known before. Starting from phosphinates derived from the phosphinamides obtained according to the invention, a whole series of phosphine oxides have been prepared by the method of Mislow et coll. (Journ. Am. Chem. Soc., 90, 4842 (1968)), particularly:
benzyl methylphenyl-phosphine oxide R(+)
benzyl methylphenyl-phosphine oxide S(−)
ethyl methylphenyl-phosphine oxide R(+)
ethyl methylphenyl-phosphine oxide S(−)
methyl o-methoxy-phenylphenyl-phosphine oxide R(+)
methyl phenyl-β-mapthyl-phosphine oxide R(+)
It will be noted that the oxazaphospholidine (F) prepared according to Example 1, all the phosphinamides of Examples 3 to 7 as well as the methyl benzylphenyl-phosphinate of Example 9 and in particular their optically-active isomers are new chemical products.

EXAMPLE 10

Preparation of (+) N-methyl-N-(1-methyl-2-iodo-2-phenyl)-ethyl(1S,2S)phosphonamide R in solution in toluene.

This compound is obtained by the action of methyl iodide on the oxazaphospholidine F of Example 1.

In a 3-neck 1-liter flask, 0.1 mole of oxazaphospholidine F is dissolved in 500 ml of toluene; 0.5 mole of methyl iodide is then added under agitation. The mixture is heated under nitrogen at 80° C. for 1 hour. After standing, a clear yellow oil separates; the toluene is evaporated and also the excess methyl iodide. The oil obtained by evaporation of the toluene is subjected to chromatography on basic alumina with ethyl acetate as the eluant. The phosphinamide is recovered after 10 150 ml fractions. The pure product has a crystalline form, the NMR characteristics of which are identical to those of the product of Example 3, but the yield of crystalline product is only about 7% as against 60% in Example 3, where the preparation has been effected without a solvent.

This example thus shows that prolonged heating at 80° C. in light leads to a bad yield in phosphinamide. The yield exceeds 60% when operation is carried out in obscurity, under nitrogen, without humidity, during 12 minutes only.

EXAMPLE 11

Preparation of a P-methyl-P-phenyl-N-methyl-N-(1-methyl-2-bromo-2-phenyl)-ethyl phosphonamide.

The preparation of this phosphinamide differs from that of Example 3 because methyl bromide is gaseous and it is not possible to react it easily with solid oxazaphospholidine.

The following operative mode is utilized.

Gaseous methyl bromide is added to 500 ml of a toluene solution of the oxazaphospholidine F of Example 1, by bubbling it in excess through the solution maintained at 80° C. for half an hour. The solvent and also the excess methyl bromide are then eliminated. The oil obtained by evaporation of the toluene is subjected to chromatography on alumina with ethyl acetate as the eluant. The yield of the reaction is lower than 5%, which confirms the conclusion of Example 10.

The phosphinamide is recovered after 10 100 ml fractions of solvent. It has the form of an oil, the NMR examination of which indicates:

| doublet | (3H) | 1.1 ppm |
|---|---|---|
| " | " | 1.9 ppm |
| " | " | 2.4 ppm |
| multiplet | (1H) | 4.5 ppm |
| doublet | " | 5 ppm |
| " | (10H) | 7.2-8 ppm |

This compound is new.

EXAMPLE 12

Preparation of (−) 3,4-dimethyl 2,5-diphenyl 1,3,2-oxazaphospholidine (2S,4R,5S) i.e. an antipode compound of the one (F) described in Example 1.

Therefore the operations of Example 1 are exactly repeated but starting from (+) ephedrine instead of (−) ephedrine.

The product thus obtained has a very good chemical and diasteroisomeric purity. Its melting point of 100° C. (recrystallization in toluene) and its NMR characteristics are the same as those of the above mentioned product F, shown in Example 1, while its $[\alpha]_D^{20°}$ is $-40°\pm5$ (c=2.5 C$_6$H$_6$) instead of $+40\% \pm 5$ for the compound F.

Now the new (−) oxazaphospholidine involved has the configuration:

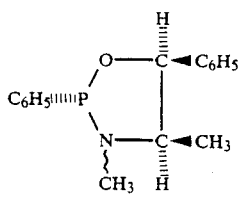

EXAMPLE 13

Preparation of (+) N-methyl N-(1-methyl 2-iodo 2-phenyl)-ethyl (1S,2S) P-methyl P-phenyl phosphinamide (R) within a solvent without heating.

Starting reagents are here the same as in Example 3, but they are dissolved in a mixture of equal volumes of benzene and cyclohexane. Thus 0.01 mol of oxazaphospholidine (F of Example 1) is dissolved in 80 ml of that mixture in a flask having a 250 ml capacity; then 0.035 mol of CH$_3$I, previously filtered on basic alumina, is added thereto. The inside of the flask is cleaned with a nitrogen stream and with this inert atmosphere it is tightly stopped, and then left for 72 hours in obscurity at room temperature. After this time, a partially crystallized oil settled at the bottom of the flask.

Now, the solvent is evaporated and the product subjected to NMR analysis which shows a yield of 84% in phosphinamide. By recrystallization in acetone, a pure product, identical to the G compound of Example 3 is obtained.

Comparison with Examples 10 and 11 thus shows a considerable improvement due to working in obscurity, without humidity at room temperature.

EXAMPLE 14

Preparing (−) N-methyl N-(1-methyl-2-iodo 2-phenyl)-ethyl (1R,2R) P-methyl P-phenyl phosphonamide (S).

This compound is the antipode of the (R) phosphinamide designated by G in Example 3. It is prepared from the (−) oxazaphospholidine of Example 12, the preparation of which has been started from (+) ephedrine.

Now, the above (S) phosphinamide is prepared in the same manner as exposed in Example 13, within the same solvent mixture of aromatic hydrocarbon and cyclane; the same yield is obtained and the same characteristics as those of the G compound, except that rotary power $[\alpha]_D^{21}$ is $-162.5°$ (c=2.5 CH$_3$OH) instead of $+162.5°$.

EXAMPLE 15

Preparation of (+) N-methyl N(1-methyl 2-bromo 2-phenyl)-ethyl (1S,2S) P-benzyl P-phenyl phosphonamide (R).

The same product is concerned as in Example 5, but the preparation is carried out in homogenous medium, cold, the reagents being previously dissolved in a mixture of 1:1 benzene/cyclohexane.

0.01 mol oxazaphospholidine (F) and 0.03 mol purified CH$_2$Br are used as a solution in 80 ml of the solvent mixture. After 7 days at room temperature, in nitrogen atmosphere, secure from light and humidity, 3.5 g of diastereoisomer crystals are recovered, which represents a yield of 60.3% in phosphinamide (R) with respect to the starting oxazaphospholidine.

EXAMPLE 16

Application of the phosphinamide G of Example 3 to the preparation of corresponding methyl phosphinate.

The preparation is similar to that of Example 7, except that it is carried out by contacting the reaction medium with an ion exchange resin as catalyst.

To 0.413 g (0.001 mol) of phosphinamide dissolved in 50 ml of methanol, 1 g of acid ion exchange resin DOWEX 50W is added, the resin having been previously washed with aqueous 10% HCl, then with water, further with methanol and dried. After 1 hour stirring at ambient temperature, the mixture is filtered and the methanol is evaporated.

The residue thus obtained is subjected to chromatography on silica with acetone as eluant; it is constituted by a methyl phosphonate having $[\alpha]_D^{20} = +47°$ (c=2 C$_6$H$_6$) and an optical purity of 82%.

The new catalyst used, the ion exchanger, bears the advantage of being easily separable by mere filtration.

EXAMPLE 17

A transformation into methyl phosphinate, in a manner identical with that of Example 16, has been carried out on the phosphinamide (R) obtained according to Example 13. Thus, methyl methyl-phenyl-phosphinate of configuration S(−) has been obtained instead of that having the configuration R(+) as in Examples 7 and 13.

This compound has $[\alpha]_D^{20} = -45°$ (c=2 C$_6$H$_6$) its optical purity being 78%.

EXAMPLE 18

Examples 3, 10 and 13 were repeated in order to show the influence of light, air and humidity on the reaction to produce phosphinamides by the process of this invention. Where purified organic halide is mentioned, this means that the halide was first filtered through active alumina (activated at 140° C. for 24 hours) so that no humidity remained in the halide. The tables below give the yield percent in phosphinamide with respect to the oxazaphospholidine used in each run.

Repetition of Example 3:

Working with solid oxazaphospholidine preheated to 110° and then reacted with CH$_3$I for 10 minutes:

| Example No. | Purified Halide | Under Nitrogen | Day Light | Yield % |
|---|---|---|---|---|
| 3 | no | yes | yes | 60 |
| 3a | yes | yes | yes | 75 |
| 3b | no | no | yes | 15 |
| 3c | yes | no | yes | 30 |
| 3d | yes | yes | no | 80 |

These results show that when working under light, it has been possible to reach a yield of 75% where there is neither humidity or oxygen. Humidity alone, although detrimental, permits a yield of 60%. Oxygen alone causes a strong drop to 30%. When humidity and air are both present, the result is very bad. Repeating experiment 3a in the absence of light gave a yield of 80%, which shows that considerable technical progress has been achieved.

Repetition of Example 10:

A solution of oxazaphospholidine in toluene at 80° C. is mixed with CH₃I and kept at 80° C. for one hour:

| Example No. | Purified Halide | Under Nitrogen | Day Light | Yield % |
|---|---|---|---|---|
| 10 | no | yes | yes | 7 |
| 10a | yes | yes | yes | 20 |
| 10b | yes | no | yes | 0 |
| 10c | no | no | yes | 0 |
| 10d | yes | yes | no | 24 |

Repetition of Example 13:

Oxazaphospholidine dissolved in a mixture of benzene and cyclohexane was reacted with CH₃I at room temperature for 72 hours:

| Example No. | Purified Halide | Under Nitrogen | Day Light | Yield % |
|---|---|---|---|---|
| 13 | yes | yes | no | 84 |
| 13a | yes | yes | yes | 60 |
| 13b | no | yes | yes | 55 |
| 13c | yes | no | yes | 10 |
| 13d | no | no | yes | 0 |

The foregoing results show that while light does not have as strong an influence as humidity and air, working in the absence of light permits obtaining a high increase in yield (84% v. 60%).

What is claimed is:

1. Process for the preparation of a phosphinamide, characterized in that an organic halide is reacted with an oxazaphospholidine in the absence of air and of humidity and in which the reaction is carried out in the absence of light.

2. Process according to claim 1, characterized in that the preparation is carried out according to the reaction:

$$
\begin{array}{c}
R^4 \\
| \\
O-C-R^3 \\
R^1-P \quad | \\
\quad \quad \\
N-C-R^5 \\
| \quad | \\
R^7 \quad R^6 \\
(A)
\end{array}
\quad + R^2X \longrightarrow
\quad
\begin{array}{c}
R^4 \\
R^2 \quad O \quad R^3-C-X \\
\backslash \parallel \quad | \\
P \\
/ \backslash \\
R^1 \quad N-C-R^5 \\
\quad | \quad | \\
\quad R^7 \quad R^6 \\
(B) \quad (C)
\end{array}
\quad (1)
$$

where the symbols $R^1$ and $R^3$ to $R^7$ designate hydrogen atoms or the same or different aliphatic, cycloaliphatic or aryl hydrocarbon groups, X is chlorine, bromine or iodine, $R^2$ in an alkyl, aralkyl, aryl, cycloalkyl or a saturated chain carrying ester, ether or ketone functional groups.

3. Process according to claim 2, characterized in that the alkyls are $C_1$ to $C_{18}$.

4. Process according to claim 3 in which the alkyls are $C_1$ to $C_4$.

5. Process according to claim 2 or 3, characterized in that at least one of $R^1$ and $R^3$ to $R^7$ represents phenyl, substituted phenyl, benzyl, napthyl, cyclopentyl or cyclohexyl.

6. Process according to claim 2, characterized in that the oxazaphospholidine, in the solid state, is heated with an excess of the organic halide.

7. Process according to claim 1, characterized in that the preparation takes place at a temperature of 10° to 100° C.

8. Process according to claim 7, wherein the temperature is 10° to 40° C.

9. Process according to claim 7, wherein the oxazaphospholidine and the organic halide are dissolved in an organic solvent.

10. Process according to claim 9, in which the solvent is a mixture of aromatic hydrocarbon and a cyclane.

11. Process according to claim 1, for the preparation of optically-active phosphinamides, characterized in that, depending upon the configuration desired for the stereoisomer to be obtained, a (+) or (−) oxazaphospholidine is used.

12. Process according to claim 11, characterized in that the antipodean stereoisomers of known absolute configuration are prepared from one or other of the two types of oxazaphospholidine, by utilizing an organic halide $R^2X$ with an oxazaphospholidine carrying a group $R^1$ on the phosphorus or a halide $R^1X$ with an oxazaphospholidine the P of which carries a group $R^2$, the two substituents $R^1$ and $R^2$ being different one from the other, $R^1$ representing hydrogen or an aliphatic, cycloaliphatic or aryl hydrocarbon group and $R^2$ representing an alkyl, aralkyl, aryl or cycloalkyl or saturated chain carrying ester, ether or ketone functional groups.

13. Process according to claim 2, wherein the product obtained is further heated with an alcohol with the addition of an alcoholysis catalyst to produce a phosphinate.

14. Process according to claim 13, in which the catalyst is an ion exchange resin.

* * * * *